United States Patent [19]

Kastrubin et al.

[11] 4,185,640

[45] Jan. 29, 1980

[54] DEVICE FOR PULSE CURRENT ACTION ON CENTRAL NERVOUS SYSTEM

[75] Inventors: Eduard M. Kastrubin; Valentin M. Mozhnikov, both of Moscow, U.S.S.R.

[73] Assignee: Moskovsky Oblastnoi Nauchno-Isslevovatelsky Institut Akusherstva I. Ginekologii, U.S.S.R.

[21] Appl. No.: 925,799

[22] Filed: Jul. 18, 1978

[30] Foreign Application Priority Data

Jul. 29, 1977 [SU] U.S.S.R. .............................. 2503851

[51] Int. Cl.² ............................................. A61N 1/34
[52] U.S. Cl. .................................... 128/421; 128/1 C
[58] Field of Search ................... 128/1 C, 419 R, 421, 128/422

[56] References Cited

U.S. PATENT DOCUMENTS

| | | | |
|---|---|---|---|
| 3,521,641 | 7/1970 | Farensbach | 128/1 C |
| 3,718,132 | 2/1973 | Holt et al. | 128/1 C |
| 3,791,373 | 2/1974 | Winkler et al. | 128/1 C |
| 3,835,833 | 9/1974 | Limoge | 128/1 C |
| 3,946,745 | 3/1976 | Hsiang-Lai et al. | 128/421 |
| 3,989,051 | 11/1976 | Nozhnikov et al. | 128/421 |

*Primary Examiner*—William E. Kamm
*Attorney, Agent, or Firm*—Steinberg & Blake

[57] ABSTRACT

According to the invention, the device for pulse current action on the central nervous system comprises switch means, each provided with regulators of pulse action parameters, such as the current pulse repetition frequency, the current pulse amplitude and the additional constant component value, the switch means being connected to a rhythmic action unit, a current pulse preamplification unit and a unit for adjusting the value of the additional constant component, and also being electrically coupled to a remote-control electroanalgesia unit or to their regulators so that according to the position of the switch means, the individual current pulse action parameters are controlled by the remote-control electroanalgesia unit and/or respective regulators taken in a prescribed combination.

1 Claim, 2 Drawing Figures

DEVICE FOR PULSE CURRENT ACTION ON CENTRAL NERVOUS SYSTEM

FIELD OF THE INVENTION

The present invention relates to devices for pulse current action upon the central nervous system.

The invention can be used to perform electroanalgesia by medical staff and/or by a patient as he or she experiences painful sensations following an operation, or as she is in pain during childbirth, etc.

BACKGROUND OF THE INVENTION

There is known a device for pulse current action upon the central nervous system. With the device operating under variable on-off time ratio conditions, current pulses are applied from a rhythmic action unit via a number of seriesly placed units, including a unit for separate adjustment of the repetition frequency and duration of current pulses, an intermittent analgesia unit, a unit for adjusting the duration of current pulses, a unit for varying the shape of current pulses, and a switch, to an input of a current pulse preamplification unit. With the device operating under constant on-off time ratio conditions, current pulses are applied from an output of the intermittent analgesia unit via the switch to the same input of the current pulse preamplification unit whose second input is connected to one of outputs of a patient protection unit having its other output connected to one of inputs of a unit for adjusting the value of an additional constant component whose other input is connected to an output of an additional constant component subunit of a power unit intended to supply power to all the abovementioned units, and electrically coupled to a remote-control electroanalgesia unit electrically coupled, in turn, to the current pulse preamplification unit whose output is connected to one of inputs of the unit for adjusting the amplitude of current pulses having its other input connected to the unit for adjusting the value of an additional constant component, whereas its outputs are respectively connected to the patient protection unit, a current pulse amplitude indicator and a mean current intensity indicator connected to an anode and a cathode attached in the neck area, under the mastoids, and in the forehead area, respectively (cf. USSR Inventor's Certificate No. 605,620, Cl. A 61N1/34).

The remote-control electroanalgesia unit can be used by medical staff or by a patient to increase or decrease such pulse current action parameters as the repetition frequency of current pulses, the current pulse amplitude and the value of the additional constant component. The device under review is such that the above-mentioned parameters can only be varied with the device operating under constant on-off time ratio conditions, wherefore the patient or medical staff are unable to increase or reduce the intensity of the pulse current action upon the central nervous system selectively and continuously, without causing any trouble to the patient, as would be desirable in the course of delivery or post-operation treatment (cf. USSR Inventor's Certificate No. 475,155, Cl. A61m21/00).

Man's response to pain is largely determined by his emotional state and his personal attitude towards pain (cf. A. V. Valdman, Yu. D. Ignatov, "Tsentralnye mechanismy boli" ("Central Mechanisms of Pain"), Leningrad, 1976, p. 138). By making it possible to change the pulse action intensity through varying one of the current parameters, such as the frequency, amplitude, on-off time ratio and the value of the additional constant component, one can produce a maximum anesthetization following a minimal action on the central nervous system. This is due to the fact that the patient is at rest emotionally, without being in fearful anticipiation of pain; this is also due to the fact that the electroanalgesia is carried out without any interruption by the patient himself.

SUMMARY OF THE INVENTION

It is an object of the present invention to provide a device for pulse current action upon the central nervous system, operating under both constant and variable on-off time ratio conditions, which could be adapted to each individual patient according to his or her reaction to pain, as well as according to a required anesthesia level prescribed by the doctor.

It is another object of the invention to provide a device for pulse current action upon the central nervous system, which would make it possible to selectively use individual pulse action parameters, such as the repetition frequency of current pulses, the amplitude of current pulses, and the value of the additional constant component, so as to vary the level of electroanalgesia.

It is a further object of the invention to provide a device for pulse current action upon the central nervous system, which would make possible a remote control of the electroanalgesia process.

The foregoing and other objects of the present invention are attained by providing a device for pulse current action upon the central nervous system, wherein, with the device operating under variable on-off time ratio conditions, current pulses are applied from a rhythmic action unit via number of seriesly placed units, including a unit for separate adjustment of the repetition frequency and duration of current pulses, an intermittent analgesia unit, a unit for adjusting the duration of current pulses, a unit for varying the shape of current pulses and a switch, to an input of a current pulse preamplification unit, whereas with the device operating under constant on-off time ratio conditions, current pulses are applied from an output of the intermittent analgesia unit via the switch to the same input of the current pulse preamplification unit whose other input is connected to one of outputs of a patient protection unit having its other output connected to one of inputs of a unit for adjusting the value of an additional constant component having its other input connected to an output of an additional constant component subunit of a power unit intended to supply power to all the abovementioned units, and is also electrically coupled to a remote-control electroanalgesia unit electrically coupled, in its turn, to the current pulse preamplification unit whose output is connected to one of inputs of the unit for adjusting the amplitude of current pulses whose other input is connected to the unit for adusting the value of an additional constant component, whereas its outputs are respectively connected to the patient protection unit, a current pulse amplitude indicator and a mean current intensity indicator connected to an anode and a cathode attached in the neck area, under the mastoids, and in the forehead area, respectively, the device being characterized, according to the invention. in that it includes switch means, each including, in turn, regulators of pulse current action parameters, s :n as the current pulse repetition frequency, the current pulse amplitude and the value of the additional constant component, respectively connected to the rhythmic action unit, the current pulse preamplification unit and the unit for adjusting the value of an additional constant component, and electrically connected to the remote-control electroanalgesia unit or to their respective regulators so that according to the position of the switch means, the individual pulse current action parameters are controlled by the remote-control electroanalgesia unit and/or the respective regulators taken in a prescribed combination.

The device for pulse current action upon the central nervous system according to the invention provides for a selective use of individual pulse current action parameters, which, in turn, makes it possible to perform electroanalgesia under optimum conditions for each patient by enabling the latter to select the most effective pulse current action parameters. Without discontinuing the electroanalgesia process and without making the patient aware of what is going on, the doctor is able to select the desired pulse action intensity by combining pulse current parameters or excluding some of these parameters with due regard for the diagnostic information on the patient's pain reaction.

BRIEF DESCRIPTION OF THE ACCOMPANYING DRAWINGS

Other objects and advantages of the present invention will become more apparent from a consideration of the following detailed description of a preferred embodiment thereof, taken in conjunction with the accompanying drawings, wherein.

DETAILED DESCRIPTION OF THE INVENTION

Figure 1:
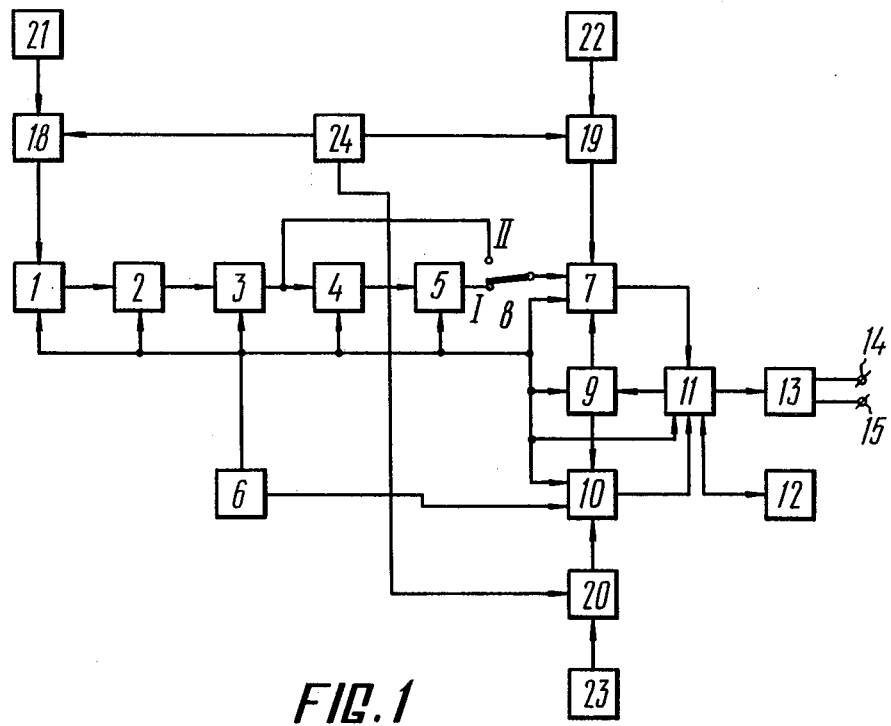
FIG. 1 is a block diagram of a device for pulse current action upon the central nervous system, in accordance with the invention.

The device according to the invention for pulse current action upon the central nervous system is described with reference to the case when said device is used for pulse current action upon the central nervous system in the course of delivery.

Referring to the attached drawings, the device comprises in series a pulse current rhythmic action unit 1 (FIG. 1), a unit 2 for separate adjustment of the repetition frequency and duration of current pulses intended to ensure an individual approach to each patient upon producing central electroanalgesia in the central nervous system of the patient, i.e. upon reaching the second level of the first stage of general electroanesthesia, an intermittent analgesia unit 3 intended to provide analgesia at each onset of labor pains, a unit 4 for adjusting the duration of current pulses, intended to produce the second level of the first stage of general electroanesthesia without any side effects on the part of the patient, and a unit 5 for varying the shape of current pulses, intended to produce the second level of the first staage of general electroanesthesia in weak patients and children. All of the above-mentioned units are connected to a power unit 6.

The device further includes a current pulse preamplification unit 7 having its input electrically coupled via a switch 8 to an output of the unit 5 for varying the shape of current pulses (position 1 of the switch 8 corresponds to the variable on-off time ratio conditions) so as to reach the second level of the first stage of general electroanesthesia, or to an output of the intermittent analgesia unit 3 (position II of the switch 8 corresponds to the constant on-off ratio conditions) so as to counteract growing pain.

A second input of the current pulse preamplification unit 7 is connected to one of outputs of a patient protection unit 9 whose other output is connected to one of inputs of a unit 10 for adjusting the value of an additional constant component, having its other input connected to an output of an additional constant component subunit of the power unit 6. An output of the current pulse preamplification unit 7 is connected to one of inputs of a unit 11 for adjusting the amplitude of current pulses, having its other input connected to the unit 10 for adjusting the value of an additional constant component. Outputs of the unit 11 are connected to the patient protection unit 9, a current pulse amplitude indicator 12 and a mean current intensity indicator 13, respectively. The means current intensity indicator 13 is connected via terminals 14 and 15 to electrodes, i.e. a split anode 16 (FIG. 2) and a split cathode 17 attached in the neck area, under the mastoids, and in the forehead area, respectively, and intended to produce the second level of the first stange of general electroanesthesia in the central nervous system of the patient.

The anode 16 and cathode 17 are of the type known to those skilled in the art, for example, of the type disclosed in U.S. Pat. No. 3,989,051, Cl. 128/421, of 1976.

Respective inputs of the current pulse preamplification unit 7 (FIG. 1), the patient protection unit 9, the unit 10 for adjusting the value of an additional constant component and the unit 11 for adjusting the amplitude of current pulses are connected to an output of the power unit 6.

The device according to the invention further includes switch means 18, 19 and 20, each provided with a regulator 21, 22 and 23, respectively, intended to control a pulse action parameter, namely, the current pulse repetition frequency, the current pulse amplitude and the value of the additional constant component, respectively. The switch means 18, 19 and 20 are respectively connected to the rhythmic action unit 1, the current pulse preamplification unit 7 and the unit 10 for adjusting the value of an additional constant component, and are electrically coupled to a remote-control electroanalgesia unit 24 or to their respective regulators 21, 22 and 23 so that according to the position of the switch means 18, 19 and 20, individual pulse current action parameters are controlled by the remote-control electroanalgesia unit 24 and/or by the respective regulators 21, 22 and 23 taken in a prescribed combination.

The individual units of the device for pulse current action upon the central nervous system in accordance with the invention are designed as follows.

The current pulse rhythmic action unit 1 (FIG. 2) is a multivibrator with an emitter capacitor built around transistors 25 and 26, resistors 27, 28, 29, 30 and 31, and a capacitor 32.

At the point of connection of the collector of the transistor 25, the base of the transistor 26 and the resistor 29, a first output of the unit 1 is connected to a capacitor 33 combined with a resistor 34 into the unit 2 for separate adjustment of the repetition frequency and duration of current pulses, which is a differentiating circuit.

A second input of the unit 1 is connected via the resistor 30 to an input of the switch means 18 which is a switch 35. In one of its positions, the switch 35 is connected to an input of the current pulse repetition frequency regulator 21 which is a variable resistor 36; in its other position, the switch 35 is connected to one of inputs of the remote-control electroanalgesia unit 24 comprising variable resistors 37, 38 and 39 interlinked by a common electromechanical regulator.

Figure 2:
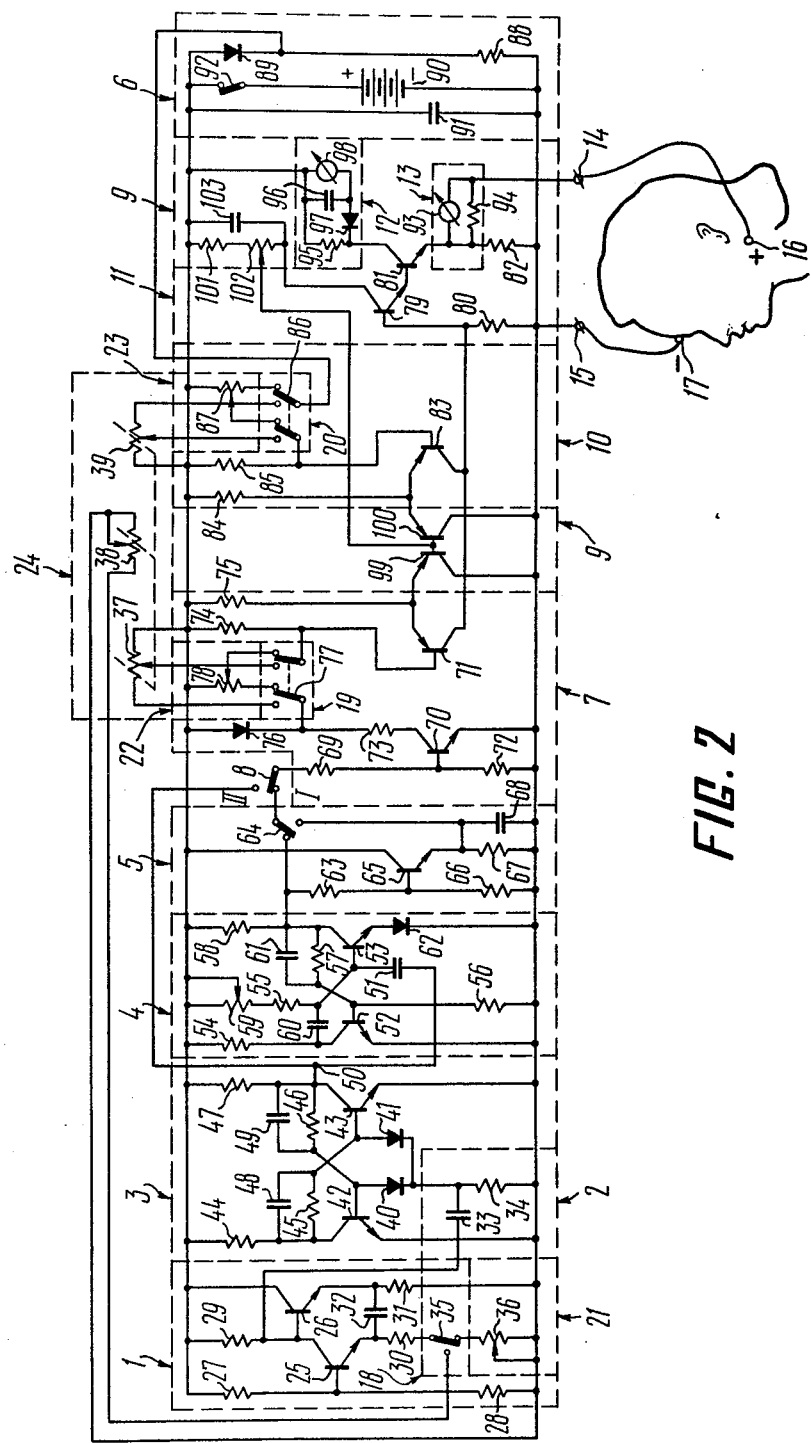
FIG. 2 is a key diagram of the device of FIG. 1.

With the switch 35 of the switch means 18 being in the position as shown in FIG. 2, continuous adjustment of the repetition frequency of the output pulse signal is carried out by moving the slide of the variable resistor 36 of the regulator 21. When the position of the switch 35 of the switch means 18 is reversed, continuous adjustment of the repetition frequency of the pulse signal is performed by the unit 24 and is determined by the position of the slide of the variable resistor 38.

At the point of connection of the resistor 34 and capacitor 33, the output of the unit 2 is connected via diodes 40 and 41 of the intermittent analgesia unit 3 to the bases of transistors 42 and 43 of said unit 3. The latter is a counting flip-flop built around the transistors 42 and 43, resistors 44, 45, 46 and 47. capacitors 48 and 49, and the diodes 40 and 41.

A periodically recurrent train of square pulses with an on-off time ratio of 2 is produced at the output of the unit 3, at the point of connection of the collector of the transistor 43, the resistors 46 and 47 and the capacitor 49. The repetition frequency of the pulses of this train is half the repetition frequency of the input signal applied from the unit 1 via the unit 2 to the unit 3.

An output 50 of the unit 3 is connected to a capacitor 51 of the unit 4 for adjusting the duration of current pulses and to the switch 8. The unit 4 is a one-shot multivibrator with collector-base capacitive couplings, built around transistors 52 and 53, resistors 54, 55, 56, 57 and 58, a variable resistor 59, capacitors 51, 60 and 61, and a diode 62. The variable resistor 59 serves for continuous adjustment of the duration of the output signal pulses, carried out within predetermined limits.

At the point of connection of the collector of the transistor 53, the resistors 57 and 58 and the capacitor 61, an output of the unit 4 is connected to a resistor 63 and a switch 64 of the unit 5 for varying the shape of current pulses acting upon the central nervous system. The unit 5 comprises a common-collector transistor 65, resistors 63, 66 and 67, a capacitor 68, and the switch 64. The emitter circuit of the transistor 65 forms an exponentially dropping trailing edge of the pulse signal. The switch 64 selects the pulse shape which may be square or with an exponentially dropping trailing edge.

The switch 8 is intended for selecting the operating conditions of the device. Position I of the switch 8 corresponds to the variable on-off time ratio conditions, whereas position II of said switch 8 corresponds to the constant on-off time ratio conditions. The switch 8 is connected to a resistor 69 of the current pulse preamplification unit 7.

The unit 7 comprises transistors 70 and 71, resistors 69, 72, 73, 74 and 75, and a diode 76. A clipper amplifier built around the transistor 70 accounts for a very stable amplitude of the output pulse signal within a broad range of variations in the supply voltage fed by the power unit 6.

The pulse signal discriminated at the diode 76 is applied, as shown in FIG. 2, via a contact of a switch 77 performing the function of the switch means 19 to a variable resistor 78 of the current pulse amplitude regulator 22. Part of this pulse signal, picked up from the slide of the variable resistor 78, is applied via a second contact of the switch 77 to the base of the transistor 71. Clearly, the amplitude of the pulse signal in the collector circuit of the transistor 71 is dependent upon the position of the slide of the variable resistor 78. When the position of the switch 77 is reversed with respect to what is shown in FIG. 2, the output signal amplitude is controlled by the variable resistor 37 of the remote-control electroanalgesia unit 24.

An output of the unit 7 is the collector of the transistor 71 and is connected to the base of a transistor 79 and a resistor 80 of the unit 11 for adjusting the amplitude of current pulses acting upon the central nervous system. The unit 11 comprises transistors 79 and 81, which account for a high input resistance and low output resistance of said unit 11, and resistors 80 and 82.

The level of an additional constant component applied to the input of the unit 11 is determined by a signal at the output of the unit 10 for adjusting the value of an additional constant component, i.e. by the signal across the collector of a transistor 83.

The unit 10 comprises a d.c. amplifier built around the transistor 83 and resistors 84 and 85. As shown in FIG. 2, the input signal is applied to the base circuit of the transistor 83 through a contact of a switch 86, which performs the function of the switch means 20, from the slide of a variable resistor 87 of the regulator 23 of the value of the additional constant component. D.c. voltage, which determines the level of the additional constant component, is applied to the variable resistor 87 of the regulator 23 through a second contact of the switch 86 of the switch means 20, being fed from the output of the additional constant component subunit of the power unit 6, which subunit is built around a resistor 88 and a voltage regulator diode 89. The power unit 6 further includes a storage battery 90, a capacitor 91 and a supply voltage cutoff switch 92.

When the position of the switch 86 of the switch means 20 is reversed with respect to the position shown in FIG. 2, the level of the additional constant component is controlled by the variable resistor 39 of the remote-control electroanalgesia unit 24.

The output signal, comprising the pulse voltage component and the constant voltage component, is picked from the output of the unit 11 for adjusting the amplitude of current pulses (i.e. from the emitter circuit of the transistor 81) and applied, via the mean current intensity indicator 13 comprising an indicator 93 and a shunting resistor 94, to the terminal 14. The negative potential of the power unit 6 is applied to the terminal 15. The way the electrodes, i.e. the anode 16 and cathode 17, are attached on the patient's head and connected to the terminals 14 and 15 is illustrated in FIG. 2.

According to FIG. 2, as the patient is connected to the terminals 14 and 15, in the collector circuit of the transistors 79 and 81 of the unit 11 there is produced a current whose intensity is determined by the total resistance at the points where the electrodes are attached to the patient's body.

The amplitude of current pulses is monitored by the current pulse amplitude indicator 12 placed in the collector circuit of the transistor 81. The unit 12 comprises a resistor 95, a capacitor 96, a diode 97 and an indicator 98 and is an amplitude (or peak) detector.

The patient is protected from current overloads by the patient protection unit 9 connected to the collector of the transistor 79 and built around transistors 99 and 100, a resistor 101, a variable resistor 102, and a capacitor 103. The variable resistor 102 serves to set the current threshold in the output circuit, i.e. to set a maximum current level in the patient circuit which is never exceeded regardless of variations in the total resistance at the points where the electrodes are attached. From the slide of the variable resistor 102, the signal is applied to the base circuits of the transistors 99 and 100 which are placed in parallel and combine with the transistor 71 of the unit 7 and the transistor 83 of the unit 10, respectively, to form two differential amplifiers. The greater the magnitude of the enable signal applied to the base circuits of the transistors 99 and 100, the lesser the amplitude of the pulse and constant signals applied to the base of the transistor 79 of the unit 11; this means that the patient protection unit 9 provides a negative feedback loop for the units 11, 7 and 10 and makes it possible to keep the current through the patient circuit at a preset level, while maintaining a low output voltage of the unit 11.

The operating principle of the device for pulse current action upon the central nervous system is as follows.

In order to produce central electroanalgesia, a mask (not shown) of rubber straps is fitted on the patient's head with the cathode 17 being attached in the forehead area, while the anode 16 is attached in the neck area, under the mastoids. A train of square pulses is produced at the output of the rhythmic action unit 1 (FIG. 1). The repetition frequency of these pulses is continuously adjusted within prescribed limits. With the switch 35 of the switch means 18 being in its first position as shown in FIG. 2, the intensity of central electroanalgesia is increased or reduced by the variable resistor 36 (FIG. 2) of the current pulse repetition frequency regulator 21; with the switch 35 being in the reverse position, this function is performed by the variable resistor 38 of the remote-control electroanalgesia unit 24.

From the output of the unit 1 (FIG. 1), the train of pulses is applied to the input of the unit 2 for separate adjustment of the repetition frequency and duration of current pulses, which makes it possible to perform central electroanalgesia for anasthesia and treatment purposes as required as required for each patient.

With the device operating under variable on-off time ratio conditions, the pulse train is applied from the output of the intermittent electroanalgesia unit 3 to the input of the unit 4 for adjusting the duration of current pulses, whereby the variable resistor 59 (FIG. 2) is used to control the duration of current pulses without producing any side effects in the patient; thus by raising the mean current intensity in the patient circuit, one can mitigate or intensify the effect of electrotranquilization attained as a result of central electroanalgesia. From the output of the unit 4, the pulse signal of a specified duration is applied via the unit 5 for varying the shape of current pulses to the switch 8, the latter being in position 1. The switch 64 of the unit 5 changes the shape of the pulses applied to the switch 8, which makes it possible to use pulse currents for anesthetizing and treating weak patients and children. With the switch 8 being in position 11, the pulse signal with a constant on-off time ratio equal to 2 is applied directly from the unit 3 to said switch 8.

From the switch 8, the pulse signal corresponding to the selected operating conditions (the constant or variable on-off time ratio conditions) is applied to the input of the current pulse preamplification unit 7 where it is amplified to a prescribed level to be then applied to the input of the unit 11 for adjusting the amplitude of current pulses. The unit 11 maintains the central analgesia at a constant level irrespective of impedance fluctuations at the points where the electrodes are attached. Depending on the position of the switch 77 of the switch means 19, the output signal amplitude is controlled by the variable resistor 78 of the current pulse amplitude regulator 22 or by the variable resistor 37 of the remote-control electroanalgesia unit 24.

Apart from the pulse signal, a prescribed value of the additional constant component is applied to the input of the unit 11 from the output of the unit 10 for adjusting the value of an additional constant component. Depending on the position of the switch 86 of the switch means 20, the additional constant component value is determined either by the variable resistor 87 of the regulator 23 or by the variable resistor 39 of the remote-control electroanalgesia unit 24.

From the output of the unit 11, the signal, which comprises the pulse and constant components, is applied via the mean current intensity indicator 13, intended for monitoring the intensity of central electroanalgesia, to the anode 16 and cathode 17 fitted on the patient's head as shown in FIG. 2.

When operating in conjunction with the unit 13, the current pulse amplitude indicator 12 makes it possible to monitor the intensity of central electroanalgesia and control the effect of electrotranquilization. The patient protection unit 9 provides a negative feedback loop for the units 11, 7 and 10, which makes it possible to maintain the prescribed mean current intensity and eliminate the effects of fluctuations in the total resistance at the electrode locations upon the mean current intensity in the patient circuit. The mean current intensity is preset by the variable resistor 102 of the patient protection unit 9.

The objects of the present invention are attained by employing the switch means 18, 19 and 20, the regulators 21, 22 and 23, and the remote-control electroanalgesia unit 24 which operates under variable on-off time ratio conditions with the switch 8 being in position 1.

Prior to inducing central electroanalgesia, the physician works out a program of pulse current action upon the central nervous system with due regard for the condition and specific pain reaction of the patient, as well as information obtained with the aid of diagnostic equipment which monitors the reactions of the basic systems of the organism such as the cardiovascular, respiratory and hemodynamics systems, to pain in the course of delivery, following an operation or in other clinical conditions when attacks of pain occur. The most rational method of remote-control electroanalgesia consists in using the switch means 18 to send signals to the remote-control electroanalgesia unit 24 so as to control the repetition frequency of current pulses.

The pulse current action upon the central nervous system must be preceded by setting the mean current intensity in the patient circuit with due regard for the required intensity of the pulse current action. This is done with the aid of the variable resistor 102 of the patient protection unit 9. The remote-control electroanalgesia unit 24 is brought into play to set the pulse repetition frequency within the range of 300 to 400 Hz, whereupon the doctor uses the regulators 23 and 22 to set the threshold values of the additional constant component and the current pulse amplitude, respectively, which is done with due regard for the patient's response. If necessary, the patient himself can increase or reduce the mean current intensity by varying the pulse repetition frequency with the aid of the unit 24. The maximum increase in the current intensity is determined by the preset mean current intensity; as stated before, the mean current intensity is set by the variable resistor 102 of the patient protection unit 9.

With the switch 8 being in position II, the device operates under constant on-off time ratio conditions. With the aid of the switch means 19, the remote-control electroanalgesia unit 24 is brought into play to control the amplitude of current pulses and thus control the increase in the mean current intensity in the patient circuit. Under such conditions, an increase in the pulse repetition frequency does not lead to an increase in the mean current intensity.

Prior to starting the pulse current action upon the central nervous system, the variable resistor 102 of the patient protection unit 9 is adjusted so as to ensure a pulse current action range of 0 to 2.5 mA.

The most rational way of operating under constant on-off time ratio conditions is to use the switch means 18 and 19 to transfer the control of the regulators 21 and 22 to the remote-control electroanalgesia unit 24. In this case the doctor controls the value of the additional constant component with the aid of the regulator 23 and with due regard for what the patient feels under the electrodes.

Apart from the patient, the remote-control electronalgesia unit 24 can be used by nurses after the optimum pulse action conditions have been set by the doctor with the aid of the variable resistor 102. As stated above, the variable resistor 102 of the patient protection unit 9 is used to set the current intensity within the range of 0 to 2.5 mA.

The remote-control electroanalgesia unit 24 makes it possible to perform central analgesia from a control board also used to control all the diagnostic equipment which monitors the vital systems of the organism.

An important advantage of the present invention resides in the possibility of an objective control of individual pulse current action parameters, as well as in that the invention makes it possible to eliminate pain and restore the functions of the organism after relieving the pain syndrome. Of special interest to researchers is the fact that the invention makes it possible to exclude or bring into play some individual current pulse action parameters without making the patient aware of what is going on.

Experiments conducted by the authors of the present invention indicate that central electroanalgesia is based upon the effect of electrotranquilization which makes it possible to control the functional state of the central nervous system for medical purposes without resorting to drugs. The experiments, conducted in a pregnancy pathology clinic and using polycardiography for diagnosis, involved 100 patients. According to the experiments, the effect of electrotranquilization improves the functional potentialities of the myocardium, mitigates arterial hypoxemia, while providing for minimum energy losses in the organism (200 observations were made with regard to oxyhemography, pneumotachometry and spirography), and eliminates hypoxia of the fetus, which made it possible for the first time to control the uterus-placenta blood circulation (300 cases).

Research conducted in this field has for the first time made it possible to assess the significance of the personal reaction of a patient in the formation of the pain sensation at the level of the central nervous system, as well as to evaluate the effectiveness of individual pulse current action parameters in different domains of clinical medicine.

The device according to the invention for pulse current action upon the central nervous system makes it possible for the first time to employ the remote-control electroanalgesia unit in clinics with the device operating under both constant and variable on-off time ratio conditions. At the same time the use of the switch means and regulators makes it possible to select an optimum combination of pulse current action parameters, which is transmitted to the remote-control electroanalgesia unit for the purposes of anesthesia and treatment.

An important feature about the invention is the fact that the process of central electroanalgesia can be controlled by both the patient and doctor. The patient is able to increase the intensity of current pulse action according to his or her subjective sensations; on the other hand, the necessity of intensifying central electroanalgesia is decided upon by the doctor with due regard for the functional state of the patient.

For greater clarity, the test of this disclosure makes use of strictly specific terminology. However, the invention does not confine itself to the notions designated by said specific terms. It is to be understood that each of the terms applies to all the equivalent units or elements operating in a similar manner and employed for similar purposes.

While a particular embodiment of the present invention has been shown and described, various modifications thereof will be apparent to those skilled in the art and therefore it is not intended that the invention should be limited to the disclosed embodiment or to the details thereof, and departures may be made therefrom within the spirit and scope of the invention as set forth in the claim.

What is claimed is:

1. A device for pulse current action upon the central nervous system, comprising:

a rhythmic action unit having a first input, a second input and an output;

a unit for separate adjustment of the repetition frequency and duration of current pulses, having a first input, a second input and an output and connected with its first input to the output of said rhythmic action unit;

an intermittent analgesia unit having a first input, a second input and an output and connected with its first input to said output of said unit for separate adjustment of the repetition frequency and duration of current pulses;

a unit for adjusting the duration of current pulses, having a a first input, a second input and an output and connected with its first input to said output of said intermittent analgesia unit;

a unit for varying the shape of current pulses, having a first input, a second input and an output and connected with its first input to said output of said unit for adjusting the duration of current pulses;

a switch electrically coupled to said output of said intermittent analgesia unit when the device operates under variable on-off time ratio conditions, and to said output of said unit for varying the shape of current pulses when the device operates under constant on-off time ratio conditions;

a current pulse preamplification unit having a first input, a second input, a third input, a fourth input and an output and connected with its first input to said switch;

a patient protection unit having a first input, a second input, a first output and a second output and connected with its first output to said third input of said current pulse preamplification unit;

a unit for adjusting the value of an additional constant component, having a first input, a second input, a third input, a fourth input and an output and connected with its first input to said second output of said patient protection unit;

a unit for adjusting the amplitude of current pulses, having a first input, a second input, a third input, a first output, a second output and a third output and connected with its first input to said output of said current pulse preamplificaton unit, with its third input to said output of said unit for adjusting the value of an additional constant component, and with its first output to said first input of said patient protection unit;

a power unit having a common output and including an additional constant component subunit having an output, said power unit being connected with its common output to the respective second inputs of said unit for separate adjustment of the repetition frequency and duration of current pulses, said intermittent analgesia unit, said unit for adjusting the duration of current pulses, said unit for varying the shape of current pulses, said current pulse preamplification unit, said patient protection unit, said unit for adjusting the amplitude of current pulses and said unit for adjusting the value of an additional constant component whose third input is connected to said output of said additional constant component subunit;

a first switch means connected to said first input of said rhythmic action unit;

a regulator of a first pulse action parameter, i.e. the current pulse repetition frequency, electrically coupled to said first switch means;

a second switch means connected to said fourth input of said current pulse preamplification unit;

a regulator of a second pulse action parameter, i.e. the amplitude of current pulses, electrically coupled to said second switch means;

a third switch means connected to said fourth input of said unit for adjusting the value of an additional constant component;

a regulator of a third pulse action parameter, i.e. the value of the additional constant component, electrically coupled to said third switch means;

a remote-control electroanalgesia unit electrically coupled to said first switch means, said second switch means and said third switch means so that according to the position of said switch means, each of said pulse action parameters is controlled by at least one of the units selected from the group consisting of said remote-control electroanalgesia unit and said regulators taken in a prescribed combination;

a current pulse amplitude indicator having an input and connected with its input to said second output of said unit for adjusting the amplitude of current pulses;

a mean current intensity indicator having an input and an output and connected with its input to said third output of said unit for adjusting the amplitude of current pulses;

electrodes, i.e. an anode and a cathode, connected to said output of said mean current intensity indicator and intended to receive said current pulses, said anode being attached in the neck areas, under the mastoids, whereas said cathode is attached in the forehead area.

* * * * *